US00PP27131P3

(12) United States Plant Patent
Tallman

(10) Patent No.: US PP27,131 P3
(45) Date of Patent: Sep. 6, 2016

(54) BLACK RASPBERRY PLANT NAMED 'NIWOT'

(50) Latin Name: *Rubus occidentalis*
Varietal Denomination: Niwot

(71) Applicant: Peter H. Tallman, Longmont, CO (US)

(72) Inventor: Peter H. Tallman, Longmont, CO (US)

( * ) Notice: Subject to any disclaimer, the term of this patent is extended or adjusted under 35 U.S.C. 154(b) by 115 days.

(21) Appl. No.: 13/999,827

(22) Filed: Mar. 25, 2014

(65) Prior Publication Data

US 2014/0338078 P1 Nov. 13, 2014

Related U.S. Application Data

(60) Provisional application No. 61/855,378, filed on May 13, 2013.

(51) Int. Cl.
*A01H 5/08* (2006.01)

(52) U.S. Cl.
USPC ..... Plt./204
CPC ..... *A01H 5/0887* (2013.01)

(58) Field of Classification Search
USPC ..... Plt./204
See application file for complete search history.

*Primary Examiner* — Keith Robinson
(74) *Attorney, Agent, or Firm* — Michelle Bos Legal LLC

(57) ABSTRACT

A new and distinct primocane-fruiting (autumn-bearing) cultivar of black raspberry, *Rubus occidentalis,* named 'Niwot'. The 'Niwot' black raspberry was created as a complex cross of two unnamed black raspberry plants collected from uncultivated areas. 'Niwot' black raspberry is capable of providing a reliable and productive crop of large black raspberries on primocanes in late summer and early autumn when there are no fresh black raspberries available from other commercial cultivars of black raspberry. 'Niwot' also provides a reliable and productive crop of black raspberries on any retained floricanes in late June and early July.

8 Drawing Sheets

Genus and species: *Rubus occidentalis.*
Variety denomination: 'Niwot'.

CROSS-REFERENCE TO RELATED APPLICATIONS

None

STATEMENT REGARDING FEDERALLY SPONSORED RESEARCH OR DEVELOPMENT

None

DESCRIPTION OF RELATED PRIOR ART

Several primocane-fruiting red raspberries are known commercially. Examples include red raspberry cultivars 'Heritage', not patented, and 'Caroline', described in U.S. Plant Pat. No. 10,412.

'Explorer' primocane-fruiting black raspberry was described in U.S. Plant Pat. No. 17,727. During evaluation trials of 'Explorer' black raspberry it was discovered that the 'Explorer' black raspberry is not self-fruitful and requires an outside source of pollen.

*The Small Fruits of New York,* by U. P. Hedrick, New York State Agriculture Experiment Station, Geneva, N.Y., 1925, lists about fifteen named varieties of primocane-fruiting black raspberry, the earliest named and most widely distributed of which was 'Ohio Everbearing' (not patented). As of 2012, there was no known source for 'Ohio Everbearing', nor was there a commercial source for any other primocane-fruiting black raspberry variety.

*Raspberries and Blackberries: Their Breeding, Diseases and Growth,* by D. L. Jennings, 1988, ISBN 0-12-384240-9, describes the existence of primocane-fruiting black raspberries in the past, including 'Ohio Everbearing', but indicates that the primocane-fruiting trait is unusual for black raspberries.

In an effort to extend the harvest season, a grower will sometimes mow down floricanes of a summer-fruiting, non-primocane-fruiting black-raspberry cultivar in early spring, to about 20 cm high, forcing fruiting laterals to grow from the remaining lower portion of the cane. Berries growing on these laterals will begin ripening after ripening is complete in a typical floricane crop. While these fruiting laterals, sometimes called "crown laterals", may appear to have some characteristics similar to fruiting primocanes, they are not very productive and they die at the end of the season, thus proving that they are not primocanes. Usually, the berries ripen on such fruiting laterals earlier than berries ripen on the primocanes of true primocane-fruiting black raspberries such as 'Explorer' and 'Niwot'.

BACKGROUND OF THE INVENTION

The 'Niwot' black raspberry is a product of a planned breeding program conducted by the inventor starting in Poughkeepsie, N.Y. and continuing in Longmont, Colo.

The 'Niwot' black raspberry originated from ancestry consisting of two selections from uncultivated areas, called W1 and W2 for purposes of this description. W1 and W2 described in the instant invention are the identical selections also designated as W1 and W2 for the description of 'Explorer' in U.S. Plant Pat. No. 17,727.

The black raspberry plant described herein as W1 was a primocane-fruiting black raspberry plant discovered by the inventor in the autumn of 1986 in an overgrown but previously landscaped residential area in Poughkeepsie, N.Y., and collected in the spring of 1988. W1 exhibited a reliable primocane-fruiting habit over the several years observed, but it had small berries and a small number of berries on each primocane, so it was not commercially useful.

The black raspberry plant described herein as W2 was the asexually propagated progeny of a black raspberry plant discovered in an uncultivated area near Rogers, Ark. and collected in the summer of 1991. W2 demonstrated an unusually large berry size for an uncultivated black raspberry. W2 did not exhibit the primocane-fruiting trait.

Selection numbered S3 was selected by the inventor in September 1993 from a population of seedlings grown in Poughkeepsie, N.Y. from open-pollinated seeds of W1. S3 was selected for producing higher quality floricane berries and larger primocane berries compared to berries of W1.

The controlled cross numbered 9866 was W2×S3 made by the inventor in Longmont, Colo. in May 1998 using floricane flowers. W2 was the seed parent, and S3 was the pollen parent. $F_1$ generation seedling numbered 9866.2 was selected by the inventor in June 2002 from a population of 9866 cross seedlings grown in Longmont, Colo. Selection 9866.2 was selected for large, attractive floricane berries.

The $F_2$ generation seedling numbered 9866.2.A that is the parent of the instant invention was grown in a cultivated area in Longmont, Colo. and selected by the inventor in July 2004 from a population of seedlings grown from open-pollinated seeds of 9866.2. Selection 9866.2.A was selected for large, attractive floricane berries. Selection 9688.2 and 9866.2.A did not exhibit the primocane-fruiting trait.

None of the numbered selections W1, W2, S3, 9866, 9866.2, and 9866.2.A was named or patented.

The black raspberry in the instant invention was selected by the inventor from a population of seedlings grown by the inventor from open-pollinated seeds of 9866.2.A in a cultivated area in Longmont, Colo. The $F_3$ generation seedling selection numbered 9866.2.A.4 was selected in June 2006 for large floricane berries. At the time of floricane selection, floricane berries weighing up to 2.4 g were observed. Selection 9866.2.A.4 was reselected in August 2006 for a productive crop of large primocane berries. At the time of primocane selection, berries weighing up to 3.7 g were observed. The selection number was abbreviated to PT-2A4 during asexual propagation and evaluation trials, then later named 'Niwot' after a village in the vicinity of the inventor's garden.

'Niwot' is distinguished from its parent 9866.2.A by its large floricane berries and its primocane-fruiting trait.

The primary market for 'Niwot' black raspberry plants is expected to be home growers, U-pick growers, farmers-market growers, and specialty-food growers for production of fresh black raspberries in both the early summer season and the late summer to early autumn season.

ASEXUAL REPRODUCTION

Asexual reproduction of the 'Niwot' black raspberry was accomplished in Longmont, Colo. by the inventor, from primocane cuttings taken in summer 2007 and grown over the winter for planting in spring 2008 and again from primocane cuttings taken in summer 2008 and grown over the winter for planting in spring 2009. After new canes sprouted from successfully rooted cuttings, additional asexual reproduction was accomplished by allowing the ends of some of these newly sprouted canes to tip root. An asexually propagated plant of 'Niwot' black raspberry planted in May 2008 produced large primocane berries in August 2008. The ability to ripen berries on primocanes and the substantially identical berry weights and druplet counts for this asexually propagated plant compared to the original selection demonstrate that the unique features of this new black raspberry are stable and reproduced true to type in the successive generation. The ability to bear fruit during the first year after being asexually propagated demonstrates that the primocane-fruiting habit is fully established and precocious in the asexually propagated plants. Additional asexual reproduction from meristem tissue culture was performed in South Deerfield, Mass. between 2008 and 2012; these meristem tissue-culture plants were produced after several generations of rooted-cutting propagation and meristem tissue-culture propagation and are also true to type.

SUMMARY OF THE NEW CULTIVAR

The following characteristics have been repeatedly observed and are determined to be the basic outstanding characteristics of 'Niwot' black raspberry as a new and distinct cultivar:

1. Reliable primocane-fruiting production of black raspberries every year, then reliable floricane fruiting the following year on the surviving portions of any floricanes that are retained.
2. Production of black raspberries that ripen in late summer and early autumn, after the normal season for floricane production of black raspberries and before an autumn freeze terminates production.
3. Large berry size, with primocane-produced berries usually exceeding a weight of 1.6 grams, and with some berries exceeding 2.4 grams each. A few berries up to 3.9 grams have been observed.
4. Large number of berries on a primocane with an unbranched primocane having over 50 berries.
5. Reliable production of good-quality berries without requiring an outside pollen source.
6. Canes hardy for overwintering without protection in USDA zone 5 to permit production of berries on floricanes the following summer.

Comparison to Existing Cultivars

The 'Niwot' black raspberry can be compared to the black raspberry cultivar 'Explorer', which was developed by the inventor and distributed for evaluation between 2005 and 2007. Compared to 'Explorer', the 'Niwot' black raspberry produces fruits reliably in the absence of an outside pollen source, whereas 'Explorer' is not fruitful in the absence of an outside pollen source. Berries of 'Niwot' are larger than 'Explorer' with a higher number of druplets, and seeds of 'Niwot' are smaller than those of 'Explorer'. Primocane berries of 'Niwot' ripen several days later than 'Explorer'. 'Niwot' does not exhibit the reduced cane prickliness characteristic of 'Explorer'.

The 'Niwot' black raspberry can be compared to the black raspberry cultivar 'Bristol' (unpatented), which was released in 1934 by the New York Fruit Testing Association in Geneva, N.Y. Compared to 'Bristol', the 'Niwot' black raspberry reliably produces fruits on primocanes, whereas 'Bristol' is not known to produce fruits on primocanes, only on floricanes. If floricanes of 'Bristol' do not survive the winter, there is no crop in the summer. Production of 'Niwot' black raspberry on primocanes may be accomplished in certain regions even after winter damage to the overwintered canes, provided the crown can be protected from winter injury.

The 'Niwot' black raspberry can be compared to the black raspberry cultivar 'Jewel' (unpatented), which was developed at Cornell University Agricultural Experiment Station, Geneva, N.Y. and released in 1973. The 'Jewel' black raspberry cultivar was not released as a primocane-fruiting cultivar and only occasionally develops flowers on primocanes. The inventor grew 'Jewel' black raspberry for several years in Longmont, Colo. and only occasionally 'Jewel' produced a limited number of berries on a single primocane. Once mature, the 'Niwot' black raspberry reliably produces fruit on most primocanes every year as grown in Longmont, Colo. The 'Niwot' black raspberry floricane-produced berries are slightly smaller and start ripening one to two weeks earlier compared to the floricane-produced berries of 'Jewel'. The 'Niwot' black raspberry demonstrates equal or better vigor compared to 'Jewel' as grown in Longmont, Colo. The 'Niwot' black raspberry demonstrates better winter hardiness than 'Jewel' in Longmont, Colo., which is USDA hardiness zone 5.

Primocanes of summer-fruiting black raspberry cultivars, for example 'Cumberland' (unpatented) or 'Bristol', arch over at mid-summer and continue growing downward rapidly in preparation for self-induced asexual propagation through tip-rooting by the end of the growing season. After the plant is mature and with good pruning, the 'Niwot' black raspberry plant only occasionally propagates itself by tip rooting. The 'Niwot' black raspberry has not been observed to spread by root suckering as is exhibited by many red raspberry cultivars.

DETAILED DESCRIPTION OF THE NEW VARIETY

The 'Niwot' black raspberry has not been observed under all possible environmental conditions. The phenotype may vary somewhat with variations in environment such as temperature, humidity, day length, light intensity, water, nutritional status, and pruning practice without, however, any variance in genotype.

The following description is based on observations made in Longmont, Colo. in the inventor's garden during the 2009 to 2013 growing seasons of asexually propagated progeny of the originally selected 'Niwot' black raspberry plant. Plants introduced from 2009 to 2011 were based on plants asexually propagated by rooting primocane cuttings. Plants introduced in 2012 were asexually propagated by meristem tissue-culture. The garden beds were prepared with native clay soil enhanced with compost mix and peat moss, along with treatment of superphosphate and soil sulfur applied according to label directions at the time of preparation and mulched with newspaper and cedar bark mulch. These plants were fertilized lightly in June 2013 and August 2013 with a water-soluble acidifying fertilizer applied from a hose-end sprayer. Productivity measurements in the instant invention were based on the 2013 crop of five plants introduced in 2012.

Additional observations and photographs were taken at the Colorado State University Boulder County Extension small-fruits evaluation garden in Longmont, Colo., hereinafter called "Extension garden". Soil in the Extension garden was prepared with approximately 0.14 cubic meters peat moss and 333 ml granular organic lawn fertilizer 8-2-1 per 4 meter row, and the soil was formed into raised beds. Seven 'Niwot' black raspberry plants were planted in a 4 meter row at a spacing of 0.6 meters apart. The row was planted in spring 2009 with plants that had been asexually propagated by rooting primocane cuttings taken in summer 2008. Plants in the row were given fertilization with water soluble organic fertilizer applied per label directions, either 5-11-11 or 20-20-20 in alternating years, on May 1, June 1, July 1 and, in some years, on August 1.

The colors are described based on the plates of The Royal Horticultural Society Colour Chart, fourth edition, 2001. Colors of certain characteristics may vary through the season, so some colors are described along with the date the color was measured.

Figure 2:
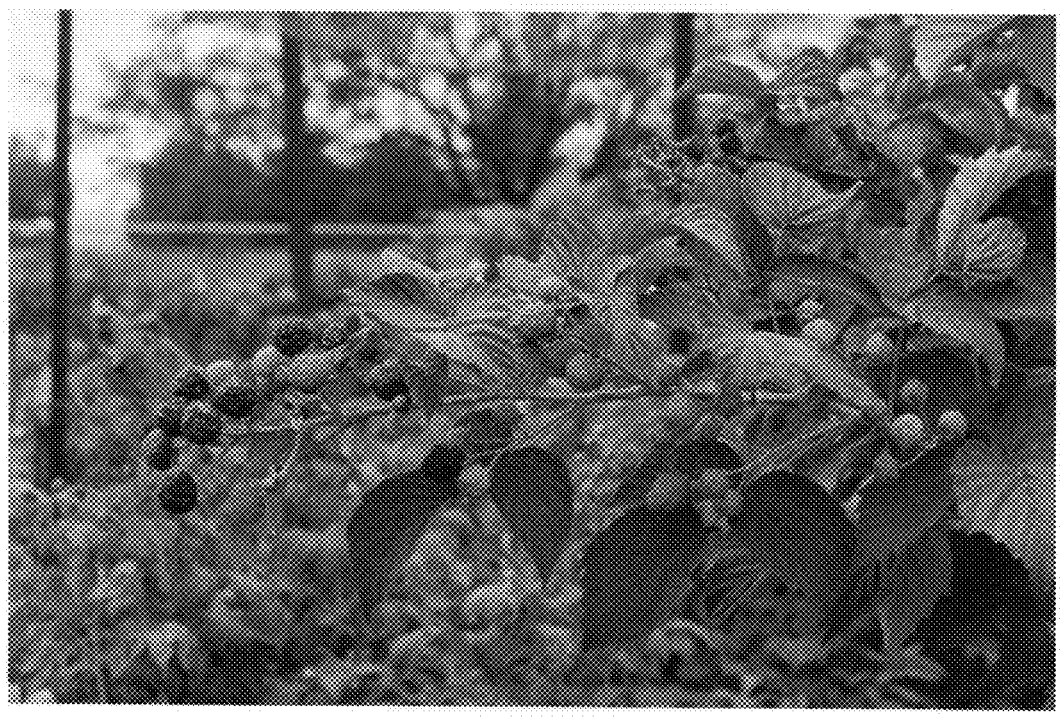
FIG. 2 is a photograph that illustrates the overall appearance of black raspberries ripening at the end of an unpruned primocane of 'Niwot' as growing in an evaluation row at Colorado State University Boulder County Extension in Longmont, Colo. The photograph was taken on Aug. 11, 2012 during the plant's fourth growing season.
Figure 3:
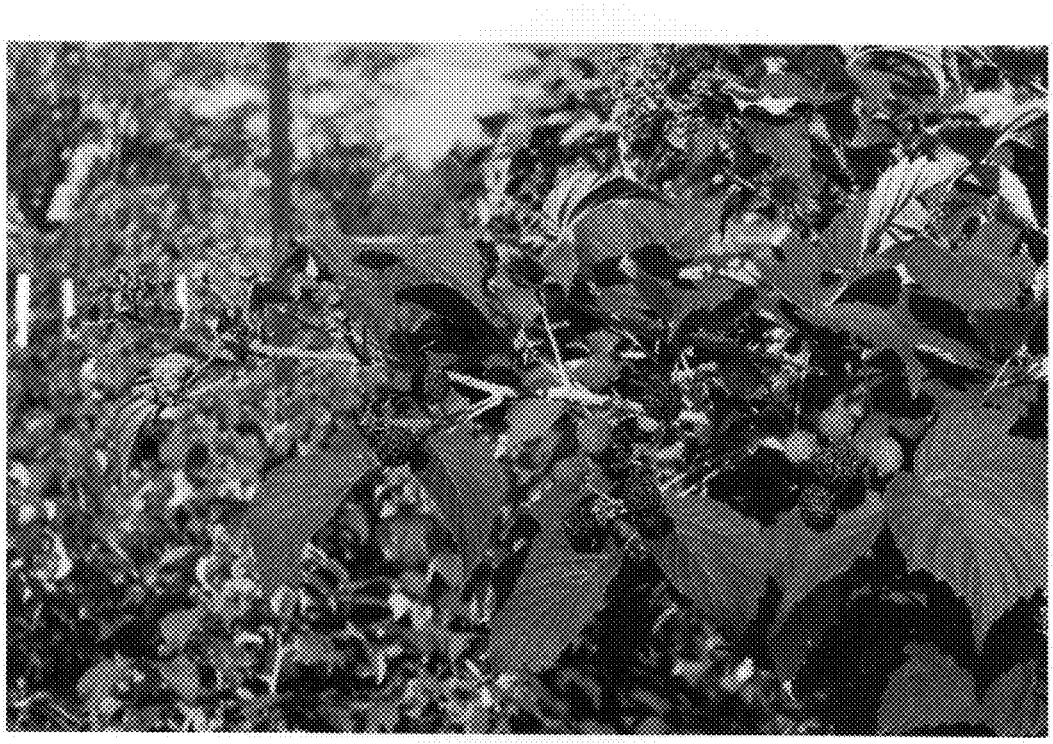
FIG. 3 is a photograph that illustrates the progression of ripening berries on a single primocane. The photograph shows the same primocane as the primocane in FIG. 2, but the photograph in FIG. 3 was taken 7 days later than the photograph in FIG. 2.
Figure 8:
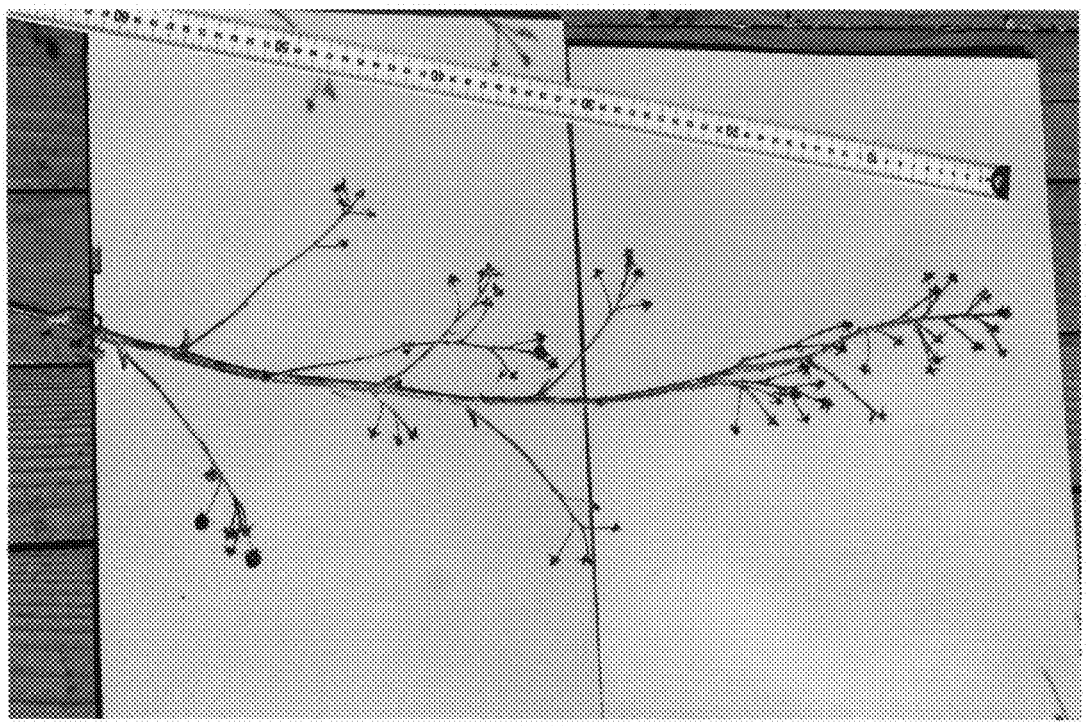
FIG. 8 is a photograph that shows the pattern of receptacles left at the end of the plant's second growing season after all berries have been picked on an unbranched primocane that had not been tip pruned. Leaves were removed to better illustrate the receptacle positions. A portion of a meter stick is included to illustrate the scale. The illustrated primocane ripened approximately 58 berries.

Primocane growth and appearance: A primocane of an established 'Niwot' black raspberry plant that emerges in the spring goes on to produce fruit in the same year. Once established, each plant normally produces several such primocanes from the same crown. In late June or early July, the primocane can be tip pruned to reduce arching and increase the number of fruits to be produced by the primocane. After tip pruning, several branches are formed from each primocane. Alternatively, the primocane can be left unpruned, which allows the ripening of berries earlier than if the canes are pruned, although there will be fewer berries on the cane. FIG. 2 shows the berries ripening on the end of an unpruned primocane on Aug. 11, 2012. FIG. 3 shows the berry ripening progression on the same primocane as FIG. 2 seven days later than FIG. 2. FIG. 8 shows the overall pattern of inflorescence on an unpruned primocane after fruiting has finished for the season. Primocane length and overall height and width of the plant depend on soil conditions, branching habit of the plant, pruning treatment, type of support, age of the plant, vigor of the plant, and competition for light with other plants or objects. As a result, these characteristics cannot readily be described as cultivar characteristics. The formation of inflorescence on the end of a primocane or primocane branch terminates further primocane extension at that site. Immature 'Niwot' plants have been observed to be less likely to form flowers than are more mature plants. Plants that have been asexually propagated using meristem tissue culture are apparently rejuvenated by the tissue-culture process and, as a result do not readily form flowers in the first growing season. A 'Niwot' black raspberry plant will occasionally propagate itself by tip rooting on the end of the primocane instead of producing flowers, but this behavior is materially inhibited by proper pruning techniques and formation of flowers once the plant is mature enough to start fruiting.

Primocanes:

*Habit.*—Semi-upright to arching.

*Emergence.*—Typically around April 15; somewhat variable by seasonal conditions in the spring.

*Length.*—Variable, depending on growing conditions and pruning treatment. On second-year plants in the inventor's garden in 2013, most unpruned canes ranged from 160 cm to 230 cm before cane growth was terminated by inflorescence.

Figure 6:
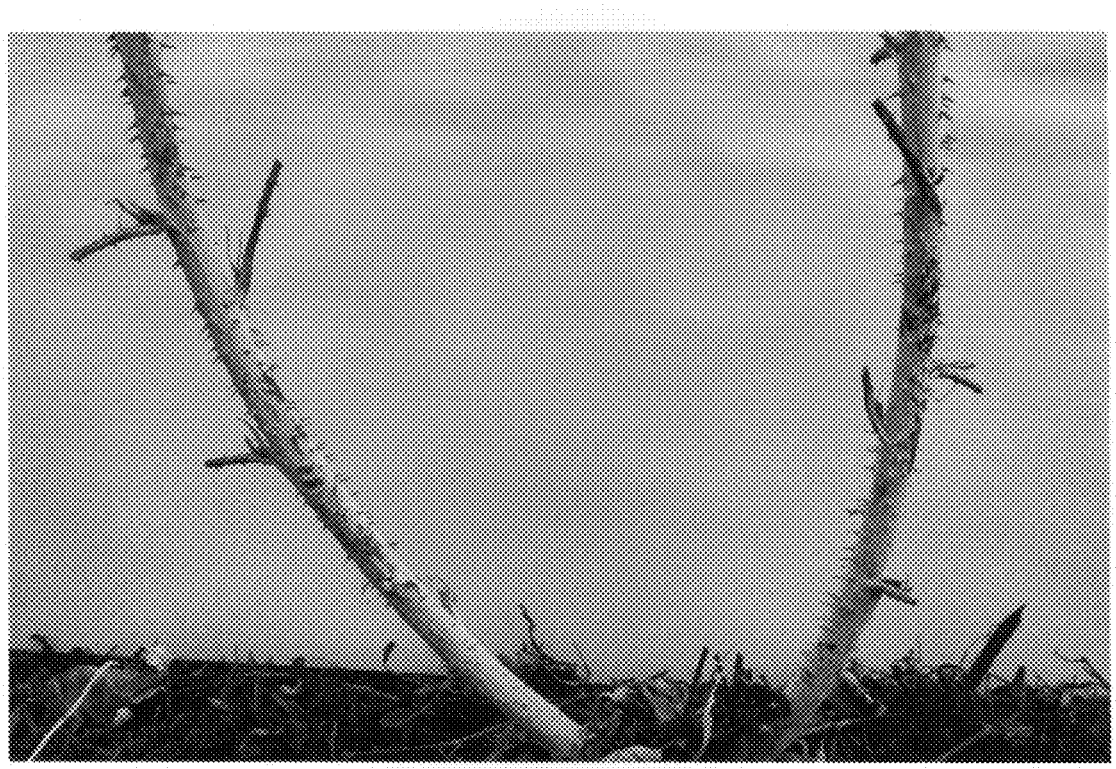
FIG. 6 is a photograph that illustrates the lower portion of two 'Niwot' primocanes as they enter winter dormancy at the end of the first growing season to show the general prickliness of the selection. This particular asexually propagated 'Niwot' plant was planted in spring 2012 from plants produced using meristem tissue culture. The photograph was taken on Nov. 19, 2012. Leaves on the primocane segments in the photograph were removed to better illustrate the prickles.

*Quantity.*—Primocane quantity depends on the age of the plant and its growing conditions. On first-year plants from tissue culture in the inventor's garden in the year of planting 2012, one or two primocanes were observed as illustrated in FIG. 6. On second-year plants in the inventor's garden in 2013, plants grew from 9 to 19 primocanes, with a mean of 14 canes. In the Extension garden of seven mature 'Niwot' plants in their fourth growing season, the mean primocane count in 2012 was 10 primocanes per plant.

*Color.*—Glaucous. Early season (May 20, 2012) waxy bloom greyed-green 194D; waxy bloom rubbed off yellow-green 144A. Mid season (Jul. 25, 2010) waxy bloom blue-green 122D; waxy bloom rubbed off yellow-green 146B. Winter dormant season (Mar. 17, 2010) waxy bloom violet-blue 91C, near violet-blue 91D and violet-blue 92D; waxy bloom rubbed off greyed-red 178A.

*Cross section.*—Nearly circular exclusive of prickles.

*Diameter.*—As measured on seven mature plants in their fourth growing season in the Extension garden, 0.6 cm to 1.4 cm at base of primocane, with a mean of 0.92 cm (November 2012).

*Prickles.*—Sharp, length typically 2.6 to 3.6 mm, diameter at base typically 0.25 to 0.5 mm tapering to point as illustrated in FIG. 6. From a primocane taken from the Extension garden, at the base, prickles small, mean 41 prickles per cm of cane; at 50 cm high, mean 2 prickles per cm of cane; within inflorescence at end of cane mean 3.2 prickles per cm of cane; dormant cane prickle color somewhat variable including greyed-orange 172C (January 2013).

Figure 7:
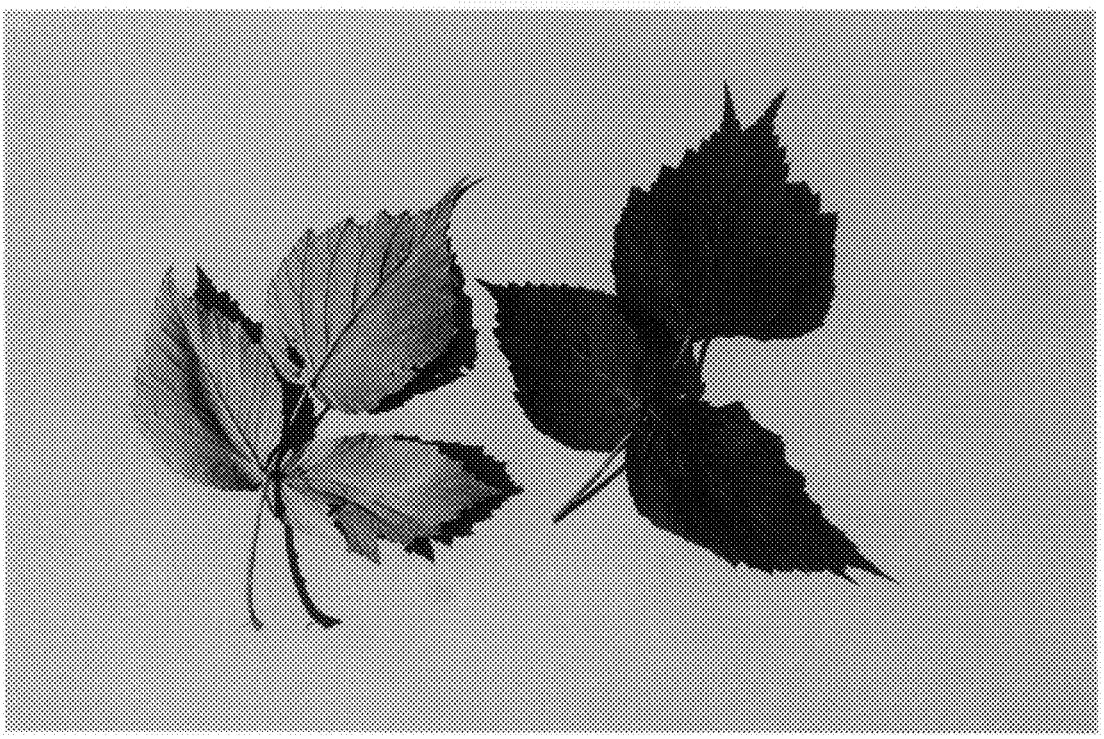
FIG. 7 is a photograph that illustrates two 'Niwot' leaves taken from a primocane on Oct. 13, 2013, one leaf showing the lower surface and the other showing the upper surface.

*Leaves.*—Odd-pinnately compound with three leaflets; not overlapped; leaflets predominantly elliptical to reniform, margins irregularly double serrate, tips acute to acuminate, and base rounded to cordate; not pubescent; upper surface green 139A (Jul. 25, 2010), lower surface color greyed-green 190B (Jul. 25, 2010); later in season lower surface color between greyed-green 198B and greyed-green 198C. FIG. 7 illustrates two leaves from a primocane.

*Apex leaflet.*—Length 9 cm to 16.6 cm, mean 11.3 cm; width 5.8 cm to 8.5 cm, mean 7.4 cm; small prickles present on underside of leaf central vein 0 to 3, mean 2.

*Side leaflet.*—Length 8.5 cm to 11 cm, mean 9.6 cm; width 4.8 cm to 7.2 cm, mean 5.8 cm; small prickles present on underside of leaf central vein 1 to 4, mean 2.7.

*Petiole.*—Mean length 6.8 cm; from 2 to 8 small prickles on the underside, mean prickle count 6; diameter 0.14 cm to 2.1 cm mean 0.18 cm.

*Petiolule.*—For side leaflets, small, 0 to 0.2 cm, diameter 0.1 cm to 0.15 cm.

*Rachis.*—For apex leaflet, length typically 2.7 to 3.9 cm; usually 2 or 3 small prickles on the underside; upper side yellow-green 146D changing to fall color red-purple 59A (Oct. 13, 2013).

*Flower.*—Unscented. Form the same as black raspberries. Flowers begin forming in early summer; in 2013 in the inventor's garden, primocane (in the second growing season) fruit buds started forming on July 15, and the first flower opened July 25. Outside surface of sepal pubescent.

*Inflorescence.*—Compound, determinate on the end of each primocane or primocane branch, flowering period variable starting from late July through August.

*Flower count.*—Count of flowering positions on a branch of a tip-pruned primocane was mean of 36 with combined overall flowering positions on a single primocane for all branches mean 183. Count of flowering positions on an unpruned primocane mean 54.

*Disease.*—No significant disease susceptibility or resistance observed compared to other red raspberry and black raspberry cultivars as grown in Longmont, Colo.

*Pests.*—No significant pest susceptibility or resistance observed compared to other red raspberry and black raspberry cultivars as grown in Longmont, Colo.

*Heat.*—Primocanes and ripening fruit observed to be tolerant of heating conditions for Longmont, Colo., which is designated as American Horticultural Society heat zones 6 and 7. During the flowering and berry ripening season, daytime temperature exceed 95 degrees Fahrenheit at times.

*Hardiness.*—Overwintering dormant primocanes are hardy for Longmont, Colo., hardiness zone 5 b (−15 degrees Fahrenheit to −10 degrees Fahrenheit average).

Figure 1:
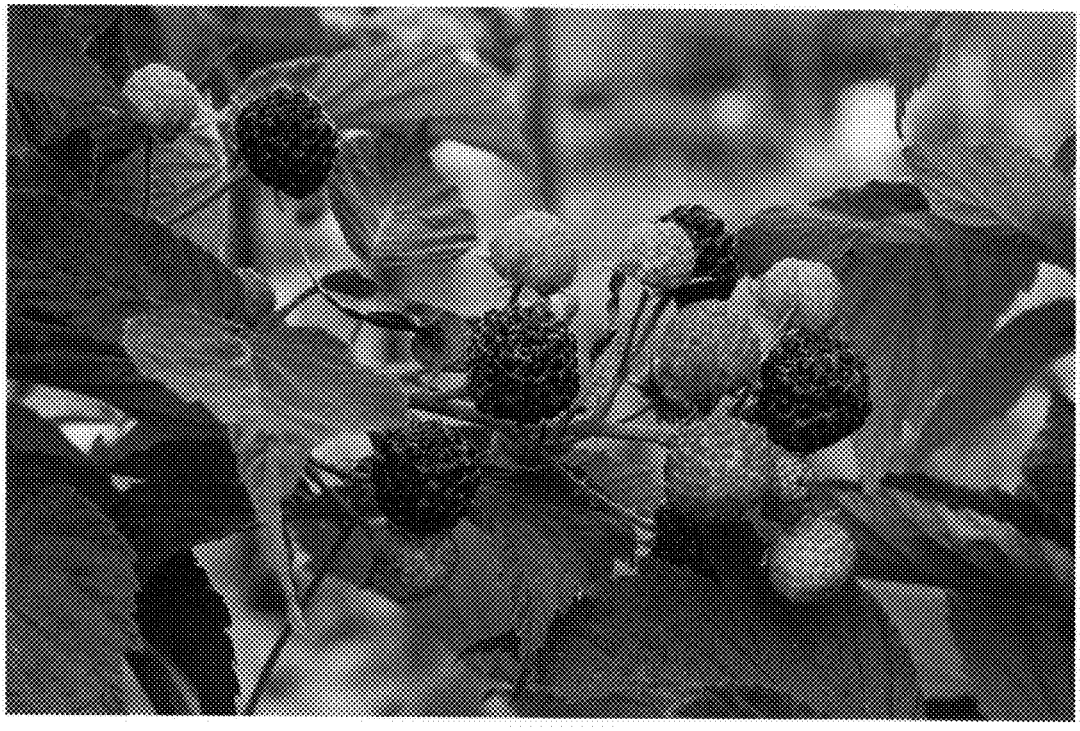
FIG. 1 is a photograph that illustrates the detail of several berries and leaves of 'Niwot' when berries are ripening at the end of an unpruned primocane of 'Niwot' as growing in an evaluation row at Colorado State University Boulder County Extension in Longmont, Colo. The photograph was taken on Aug. 11, 2012 during the plant's fourth growing season.

Ripening schedule of primocane berries: Timing of primocane berry ripening depends on floricane treatment, primocane tip pruning, plant age, and weather and growing conditions. Eliminating floricanes before growth starts in the spring will frequently cause primocane berry ripening earlier than if floricanes are retained to fruit in the summer. Tip pruning to increase the berry count on a primocane will delay the start of ripening of berries on the primocane, with the particular ripening date somewhat dependent on the tip pruning date. In the inventor's garden in 2010, a primocane cane tip pruned on June 21 started ripening berries on August 13, or about 53 days after tip pruning. In the inventor's garden, berries on a cane tip pruned on Jul. 1, 2013 started ripening berries on Sep. 21, 2013, or about 82 days from tip pruning. Regular fertilization can encourage berry ripening earlier than on weak plants. On a single plant of several primocanes, several different ripening schedules can be induced by tip pruning different primocanes at different times. FIG. 1 shows the details of berries ripening on the end of an unpruned primocane in the Extension garden on Aug. 11, 2012.

Primocane berries:

*Fruit.*—Berries soft, druplets glossy.

*Size.*—Large; earlier ripening berries tend to be larger than later ripening berries on the same primocane. Average of measurements taken from berries harvested from the inventor's garden on Sep. 8, 2013: mean weight 3.1 g, with most berries exceeding 2.7 g, and a few berries up to 3.9 g. Later in the season, on September 29, mean berry weight 2.6 g with most berries exceeding 2 g. Berries harvested at the Extension garden on Aug. 18, 2012: mean weight 1.9 g; most berries weighed more than 1.6 g, and a few berries reached 2.3 g. At the Extension garden in 2013, the first primocane berries ripened on August 24.

Figure 5:
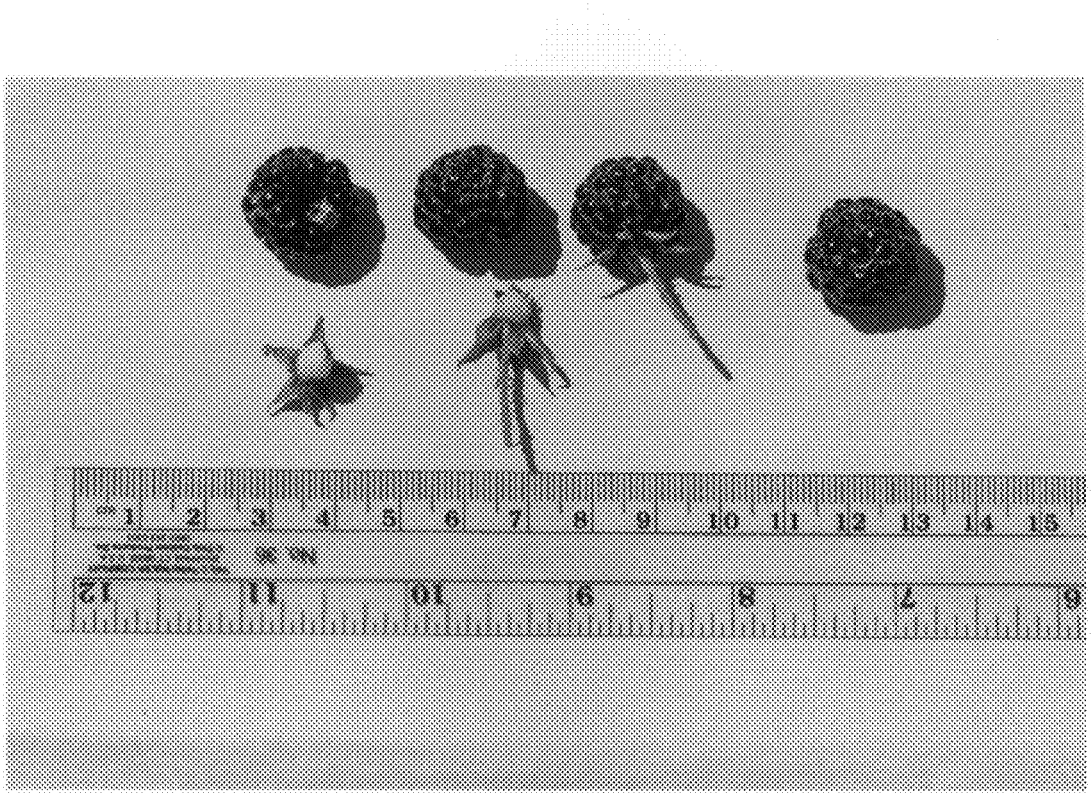
FIG. 5 is a photograph that illustrates four 'Niwot' berries together with two receptacles left behind when the ripe berries were picked; photograph was taken on Aug. 18, 2012 of berries grown in the evaluation row at Colorado State University Boulder County Extension in Longmont, Colo.

*Shape.*—Overall near truncated sphere, usually truncated slightly below the equator, so slightly larger than a hemisphere; shape of several berries is illustrated in FIG. 1 and FIG. 5. Upon careful measurement, may be found toward truncated ellipsoid, also truncated slightly below the equator. Berry surface as illustrated in FIG. 5 consists of the truncated-spherical exposed portions of many interlocked drupelets, some dimpled, each truncated above the equator; overall bumpy surface appearance usually associated with raspberries. On berries taken from the inventor's garden on Sep. 29, 2013 the mean height was 1.7 cm, mean diameter 1.8 cm.

*Druplets.*—Sampled berries taken from the inventor's garden on Sep. 29, 2013 exhibited from 110 to 152 druplets per berry, with a mean of 123 druplets.

*Receptacle.*—Receptacle left behind when the ripe berry is picked cylindrical to conical, rounded apex; receptacle size and shape also describe the size and shape of the berry cavity. FIG. 5 illustrates the receptacle shape.

*Seeds.*—Average weight 2.0±0.1 mg; measured after separating the seeds from the pulp with water in a blender then drying for 48 hours at room temperature; measured in a batch of 100 seeds.

*Acidity.*—pH 3.6±0.1 measured using a pH meter on pulp extracted from crushing ripe berries and straining to remove seeds.

*Sweetness.*—Soluble solids brix 11.5±0.5° as measured with a refractometer on pulp extracted from crushing ripe berries and straining to remove seeds.

*Flavor.*—Characteristic black raspberry flavor.

Figure 4:
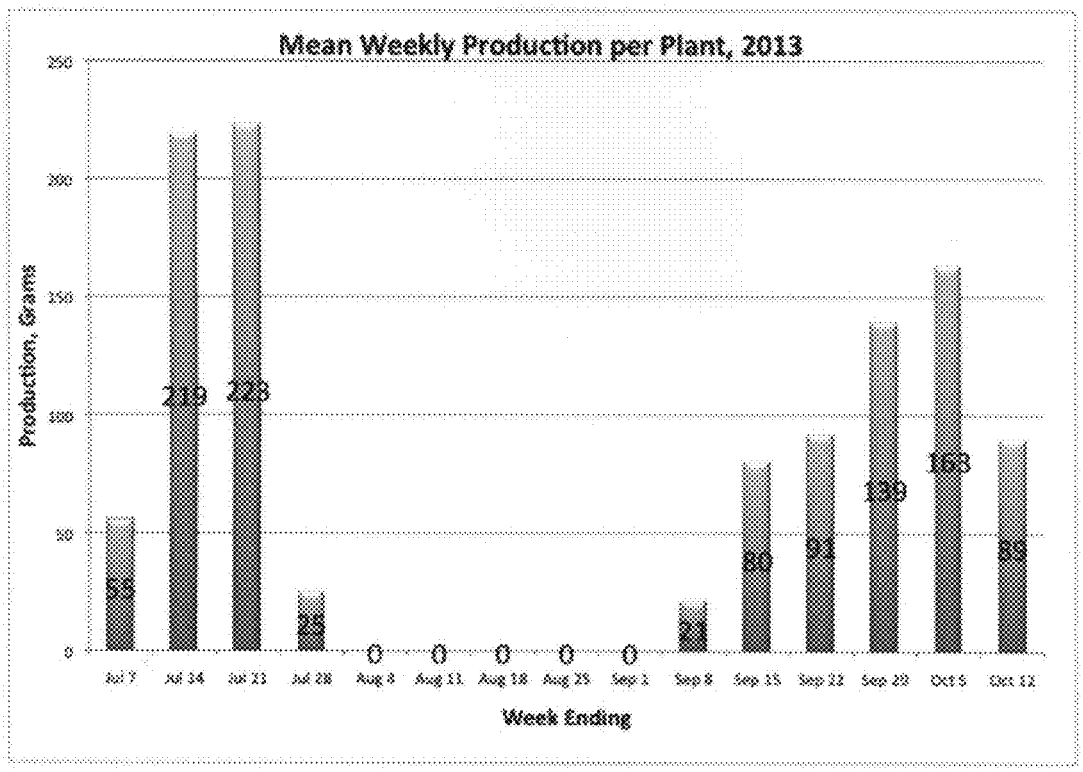
FIG. 4 is a chart that illustrates the mean weekly berry crop production per plant in 2013 in the inventor's garden of five second-year 'Niwot' black raspberry plants; the chart shows production in both floricane and primocane ripening seasons.

*Productivity.*—In the inventor's garden in 2013, for five plants, the mean floricane crop per plant for 2013 was 583 grams. The floricane and primocane crop sizes are illustrated together graphically in FIG. 4.

*Heat.*—Tolerant of heating conditions for Longmont, Colo., which is designated as American Horticultural Society heat zones 6 and 7. Flowers and ripening berries observed to be tolerant of daytime temperature of 95 degrees Fahrenheit or more before harvest.

*Hardiness.*—Ripening primocane berries are frost tender.

Floricane and floricane fruiting: Much of the upper portion of the primocane that forms primocane flowers and berries in the autumn dies at the end of the growing season. The rest of the primocane goes dormant in late autumn then overwinters to become a floricane the next spring when fruiting laterals form on the surviving portion of retained canes. In the early spring, canes are typically pruned to remove the portion of the cane that had fruited as primocanes the previous autumn and to create a uniform cane height and branch length in the row. As a result, floricane length is not a descriptive characteristic of the cultivar. Berries ripen on floricane fruiting laterals through mid-summer. Following the end of floricane fruit ripening, the floricanes gradually decline and die. Unless otherwise noted, floricane and floricane fruit and characteristics are not materially different from primocane and primocane fruit characteristics.

Floricanes:

*Cane color.*—Glaucous; cane with waxy bloom violet 85C; waxy bloom rubbed off greyed-purple 187A (May 20, 2012) to greyed-purple 186C (Jul. 25, 2010).

*Laterals.*—Length variable from 17 cm to 45 cm, mean 30 cm; mean diameter 0.3 cm; lateral count per floricane variable, typically 12 to 19 per floricane; color near yellow-green 144B and yellow-green 145A.

*Leaves.*—Carried on fruiting laterals; odd-pinnately compound with three leaflets, not overlapped; leaflets predominantly elliptical to reniform, margins irregularly double serrate, tips acute to acuminate, and base rounded to cordate; upper side of leaf green 137A to green 139A; underside of leaf greyed-green 194A; leaflets not pubescent. Side leaflet mean length 6.2 cm, width 3.4 cm, from zero to two small prickles on lower surface central rib. Terminal leaflet length 6.9 cm, width 4.2 cm.

*Petiole.*—Mean length 5.8 cm, mean diameter 0.12 cm, usually having 2 to 6 small prickles on the underside, with a mean of 4 prickles.

*Petiolule.*—For side leaflets, small 0 to 0.2 cm.

*Rachis.*—For terminal leaflet, mean length 2.2 cm, usually having 0 to 2 small prickles on the underside with a mean of 1 prickle. For side leaflets, mean length 0 cm to 0.2 cm.

*Productivity.*—For five plants sampled in their second growing season sampled in the inventor's garden, the mean total floricane crop per plant for 2013 was 522 g. The floricane and primocane crop productivities are illustrated together graphically in FIG. 4.

*Inflorescence.*—Fruiting lateral inflorescence mean 12 flowers; typically 1 to 3 flowers per leaf node on fruiting lateral; flowers on apex inflorescence 5 to 12 flowers, mean 8.

*Flowers.*—Unscented. Morphology typical for most black raspberry cultivars. In 2010, first flowers open May 29, most flowers completed blooming June 16. In 2011, first flowers opened May 26, most flowers completed blooming June 17; sepals pubescent; flower color sepals outside yellow-green 145A, inside green 147C; petals — quantity 5, color white 155C.

Floricane berries:

*Size.*—In the inventor's garden in 2013, first berries harvested Jul. 4, 2013 averaged 2 g. In 2010, first berries ripened on July 5, which was 40 days after first flowers open. Berries harvested Jul. 8, 2010 weighed an average of 2 g, with most berries exceeding 1.6 g. Mean diameter 1.7 cm, mean height 1.4 cm.

*Druplets.*—Mean number of druplets per berry 106.

*Acidity.*—pH 3.4±0.1 measured using a pH meter on pulp extracted from crushing ripe berries and straining to remove seeds.

*Sweetness.*—Soluble solids brix 12±0.5° as measured with a refractometer on pulp extracted from crushing ripe berries and straining to remove seeds.

*Color.*—Near blue N92A and purple N77A; smear of ripe berry pulp on white plate red 45B.

*Seed weight.*—Mean 1.6±0.1 mg; measured after separating the seeds from the pulp with water in a blender then weighed after drying for 48 hours at room temperature; seeds weighed as a batch of 100 seeds.

I claim:

1. A new and distinct primocane-fruiting black raspberry plant substantially as described and illustrated herein.

* * * * *